US009308073B2

(12) United States Patent
Fischer, Jr. et al.

(10) Patent No.: US 9,308,073 B2
(45) Date of Patent: Apr. 12, 2016

(54) VENA CAVA FILTER WITH DUAL RETRIEVAL

(75) Inventors: Frank J. Fischer, Jr., Bloomington, IN (US); Aaron Weeks, Plano, TX (US); Darrell Talbert, Bloomington, IN (US); Richard J. Sacco, Graceton, PA (US); William Teat, Bloomington, IN (US); Gerald L. Williams, Salt Lake City, UT (US); Diana Wu, Bloomington, IN (US); Susan Gall Sahlgren, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 672 days.

(21) Appl. No.: 13/611,917

(22) Filed: Sep. 12, 2012

(65) Prior Publication Data

US 2014/0074146 A1 Mar. 13, 2014

(51) Int. Cl.
*A61M 29/00* (2006.01)
*A61F 2/01* (2006.01)

(52) U.S. Cl.
CPC ............. *A61F 2/01* (2013.01); *A61F 2002/011* (2013.01); *A61F 2002/016* (2013.01); *A61F 2230/005* (2013.01); *A61F 2230/0078* (2013.01)

(58) Field of Classification Search
None
See application file for complete search history.

(56) References Cited

U.S. PATENT DOCUMENTS

| 4,619,246 | A | * | 10/1986 | Molgaard-Nielsen et al. ........................ 128/899 |
| 5,324,304 | A | | 6/1994 | Rasmussen |
| 5,370,657 | A | | 12/1994 | Irie |
| 6,306,163 | B1 | | 10/2001 | Fitz |
| 6,447,530 | B1 | | 9/2002 | Ostrovsky et al. |
| 6,872,217 | B2 | | 3/2005 | Walak et al. |
| 7,033,376 | B2 | | 4/2006 | Tsukernik |
| 7,857,826 | B2 | | 12/2010 | Eskuri et al. |
| 8,029,529 | B1 | | 10/2011 | Chanduszko |
| 2005/0131451 | A1 | | 6/2005 | Kleshinski et al. |
| 2005/0159771 | A1 | | 7/2005 | Petersen |
| 2005/0288704 | A1 | | 12/2005 | Cartier et al. |
| 2010/0016882 | A1 | | 1/2010 | Lapid |
| 2010/0160954 | A1 | | 6/2010 | Osborne |
| 2011/0106133 | A1 | * | 5/2011 | O'Connell et al. ........... 606/200 |
| 2011/0125180 | A1 | | 5/2011 | Tripp et al. |
| 2013/0103073 | A1 | * | 4/2013 | Honeycutt ................ A61F 2/01 606/200 |

FOREIGN PATENT DOCUMENTS

WO    WO 01/15630 A1    3/2001

OTHER PUBLICATIONS

European Search Report Dated Nov. 27, 2013.
European Office Action dated Dec. 10, 2015.

* cited by examiner

*Primary Examiner* — Robert Lynch
(74) *Attorney, Agent, or Firm* — Brinks Gilson & Lione

(57) ABSTRACT

An intravascular filter assembly has an expanded state for capturing thrombi in a patient's blood vessel and a collapsed state for removal from the patient's blood vessel. The filter assembly includes a fixed hub defining a tubular portion, a plurality of struts extending from a first axial side of the tubular portion of the fixed hub, and an axially movable hub. The struts have an expanded configuration and a collapsed configuration. The axially movable hub has a first position radially surrounding at least an axial portion of the tubular portion and a second position axially spaced apart from the fixed hub along the struts. The struts are in the collapsed configuration when the movable hub is in the second position. A first coupling member extends from the first axial side from the movable hub; and a second coupling member extends from a second axial side opposite the first axial side.

20 Claims, 3 Drawing Sheets

VENA CAVA FILTER WITH DUAL RETRIEVAL

BACKGROUND OF THE INVENTION

The present invention relates to medical devices. More particularly, the invention relates to a removable vena cava clot filter that can be percutaneously placed in and removed from the vena cava of a patient.

A need for filtering devices arises in trauma patients, orthopedic surgery patients, neurosurgery patients, or in patients having medical conditions requiring bed rest or non-movement. During such medical conditions, filtering devices are inserted to prevent thromboses in the peripheral vasculature of patients when thrombi break away from the vessel wall, risking downstream embolism or embolization. For example, depending on the size, such thrombi pose a serious risk of pulmonary embolism wherein blood clots migrate from the peripheral vasculature through the heart and into the lungs.

The benefits of a vena cava filter have been well established. After deployment of a filter in a patient, proliferating intimal cells begin to accumulate around filter struts that contact the wall of the vessel. After a length of time, such ingrowth poses difficulties for removal of the filter. In addition, typical filter deployment and retrieval are directionally dependent. For example, filters inserted using a femoral approach may require the retrieval to take place through a jugular approach. A vena cava filter that can be easily retrieved independent of the orientation of the filter deployment within the vessel

SUMMARY OF THE INVENTION

According to one aspect of the invention, an intravascular filter assembly has an expanded state for capturing thrombi in a patient's blood vessel and a collapsed state for removal from the patient's blood vessel. The filter assembly includes a fixed hub defining a tubular portion, a plurality of struts extending from a first axial side of the tubular portion of the fixed hub, and an axially movable hub. The struts have an expanded configuration and a collapsed configuration. The axially movable hub has a first position radially surrounding at least an axial portion of the tubular portion and a second position axially spaced apart from the fixed hub along the struts. The struts are in the collapsed configuration when the movable hub is in the second position. A first coupling member extends from the first axial side from the movable hub; and a second coupling member extends from a second axial side opposite the first axial side. The opposite coupling members allow for retrieval from both the jugular side and the femoral side.

According to another aspect of the invention, the fixed hub may have an axial passage formed therethrough. Such an axial passage allows access to the interior of the filter assembly through the fixed hub.

According to a further aspect of the invention, an elongated push tool with a tip having a diameter greater than the axial passage and smaller than a distance of opposing struts adjacent the fixed hub may be used for holding the fixed hub in an axial location while the movable hub is moved relative to the fixed hub.

According to another aspect of the invention, the filter assembly may further comprise a stopper preventing the movable hub from moving past the tubular portion on the second axial side. The stopper may, for example, be an annular collar formed on the fixed hub adjacent the tubular portion.

According to another aspect of the invention, the filter assembly may further comprise a retainer limiting a distance of travel of the movable hub along the struts. Thus, the retainer may define the second position of the movable hub.

According to another aspect of the invention, the retainer may be formed by a jugular hook forming the second coupling member. The jugular hook thus may perform a dual function, thereby simplifying the construction of the filter assembly. For example, the jugular hook may have an axial length determining the second position of the movable hub.

According to yet another aspect of the invention, each of the struts may have a first curved portion bending the strut away from a longitudinal axis of the filter and a second curved portion bending the strut toward the longitudinal axis of the filter. For struts of this shape, the second position of the movable hub is preferably at least as far away from the fixed hub as the first curved portion of each strut.

According to another aspect of the present invention, where the filter assembly has a fixed hub defining a tubular portion; a plurality of struts extending from a first axial side of the tubular portion of the fixed hub, the struts having an expanded configuration when the filter is in an expanded state and a collapsed configuration when the filter is in a collapsed state; an axially movable hub having a first position radially surrounding at least an axial portion of the tubular portion and a second position axially spaced apart from the fixed hub along the struts, the struts being in the collapsed configuration when the movable hub is in the second position; and a first coupling member extending from the first axial side from the movable hub; a method of removing an intravascular filter assembly from a body vessel comprises the steps of inserting a recovery sheath with a lumen into the body vessel from the first axial side; placing a recovery tool within the lumen of the recovery sheath and moving it distally toward the filter assembly; engaging the first coupling member with the recovery tool; placing a push tool within the lumen of the recovery sheath and moving it distally toward the filter assembly; abutting and retaining the fixed hub at a fixed location; pulling the movable hub off the tubular portion along the struts until the movable hub is in the second position and the struts are in the collapsed configuration; proximally removing the push tool; causing a relative movement between the filter assembly and the recovery sheath in a direction that causes the filter assembly to enter the lumen of the recovery sheath; and proximally removing the recovery sheath including the filter assembly.

The push tool and the recovery sheath may be removed simultaneously or consecutively.

According to another aspect of the invention, if the filter assembly further includes a retainer limiting a movement of the movable hub along the struts and thereby defining the second position of the movable hub, the movable hub is moved until the retainer limits the movement.

According to another aspect of the invention, the retainer may be a jugular hook with a dual function that limits the movement of the movable hub by abutting the fixed hub.

Further aspects, features, and advantages of the invention will become apparent from consideration of the following description and the appended claims when taken in connection with the accompanying drawings.

DETAILED DESCRIPTION OF THE DRAWINGS

The following drawings are included for illustrative purposes only and are not intended to limit the scope of the present invention. The drawings are of a purely schematic nature and are not drawn to scale. In particular, any elongated elements such as struts and wires are shown shortened in FIGS. 2 and 3.

Figure 1:
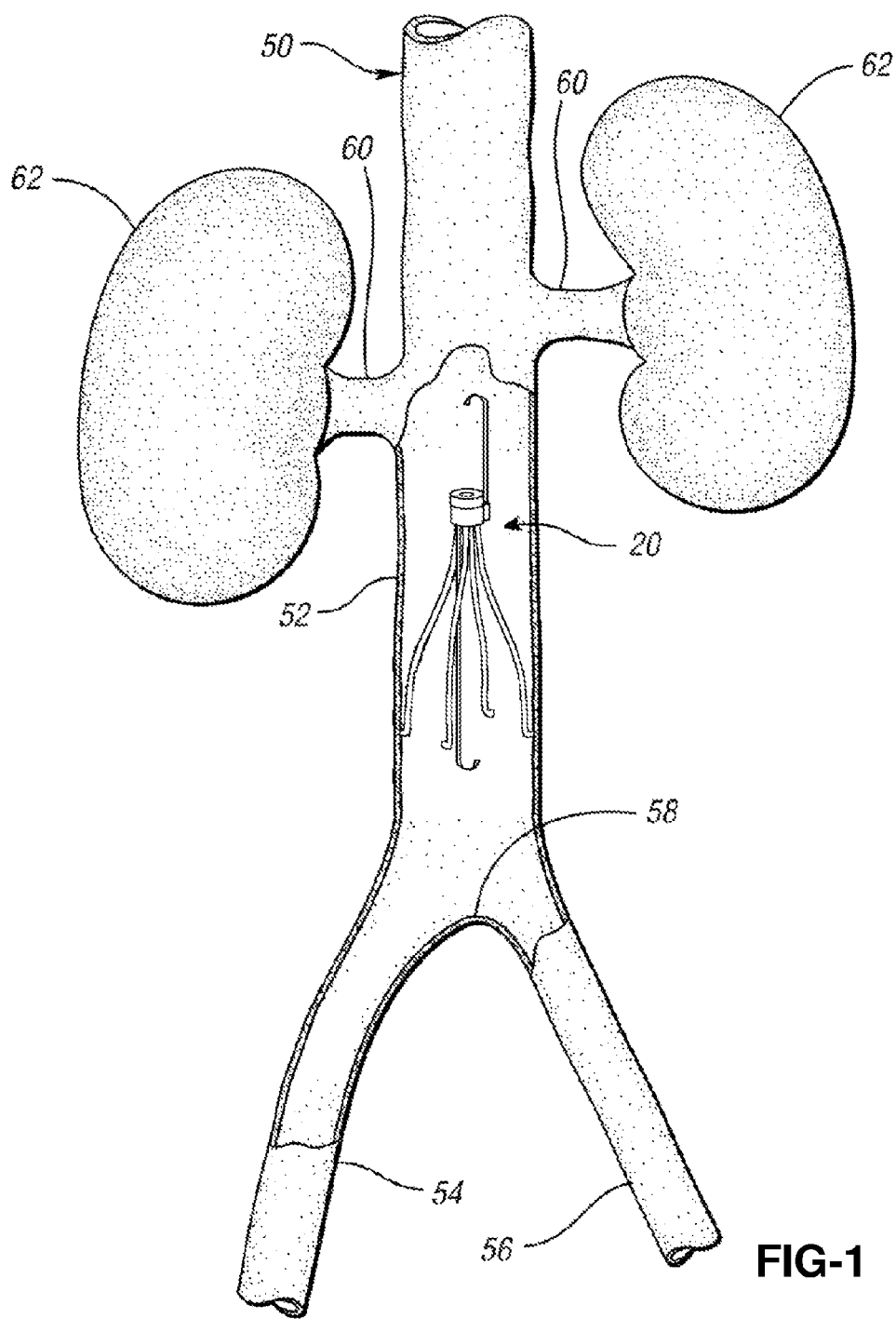
FIG. 1 is an illustration of the anatomy of the renal veins, the femoral veins, and the vena cava, in which one embodiment of a vena cava filter of the present invention is deployed.

In accordance with a first embodiment of the present invention, FIG. 1 illustrates a vena cava filter 20 implanted in a vena cava 50 for the purpose of lysing or capturing thrombi carried by the blood flowing through the femoral veins 54 and 56 toward the heart and into the pulmonary arteries. As shown, the femoral veins 54 and 56 from the legs merge at juncture 58 into the vena cava 50. The renal veins 60 from the kidneys 62 join the vena cava 50 downstream of juncture 58. The portion of the vena cava 50, between the juncture 58 and the renal veins 60, defines the inferior vena cava 52 in which the vena cava filter 20 has been percutaneously deployed through one of the femoral veins 54. Preferably, the vena cava filter 20 has a length smaller than the length of the inferior vena cava 52.

Figure 2:
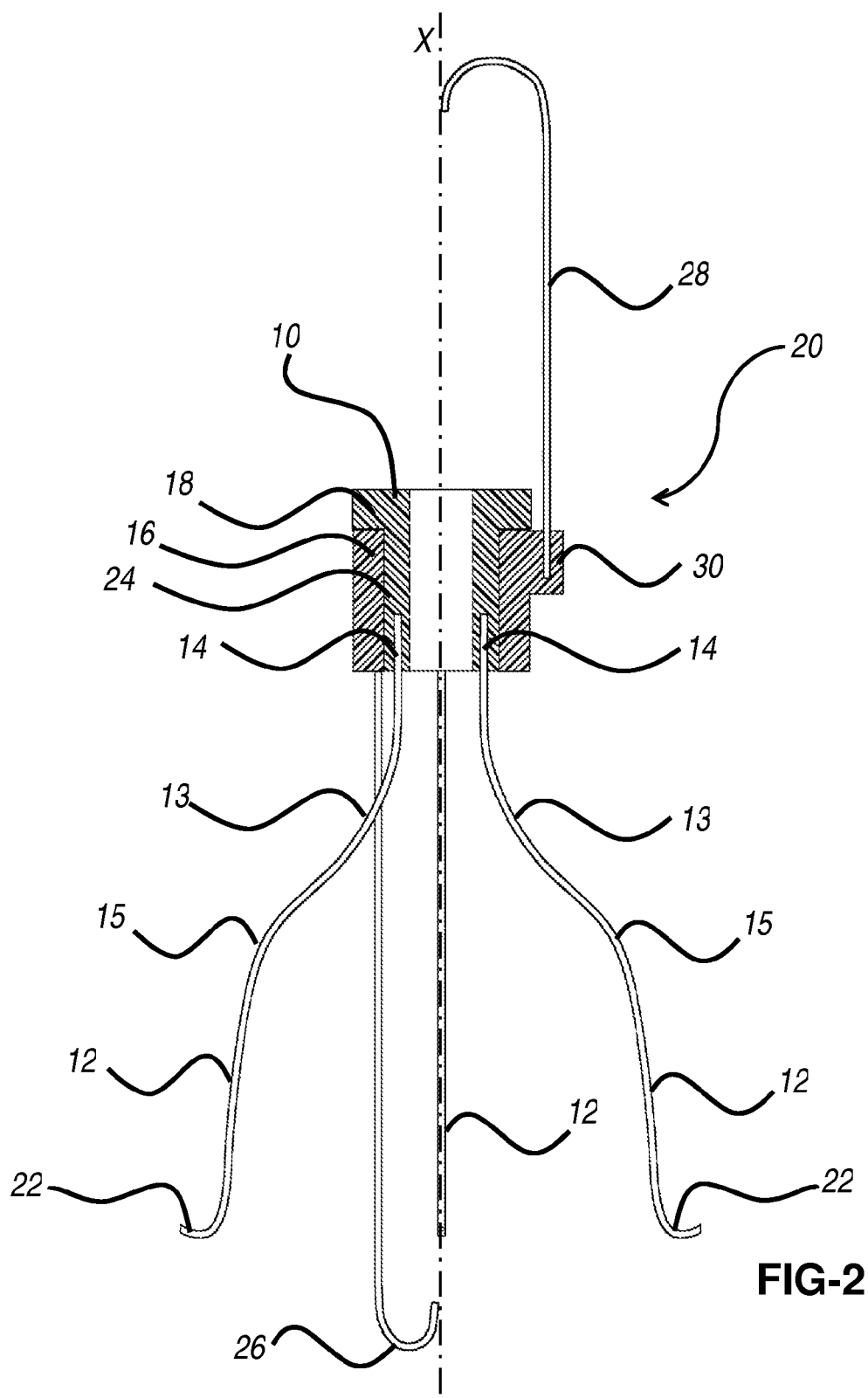
FIG. 2 is a cross-sectional view of one embodiment of the vena cava filter of the present invention in an expanded configuration.

One embodiment of the present invention will be discussed with reference to FIGS. 2 and 3 in which filter 20 is shown. FIG. 2 illustrates a cross-section of filter 20 in an expanded configuration. The filter 20 comprises four struts 12 each having fixed ends 14 that are secured in a fixed hub 10. In the cross-sectional view of FIG. 2, only three of the four struts 12 are visible. Any other number of struts, such as two, three, five, or six, is also within the scope of the invention. While a greater number of struts may be suited to filter thrombi of a smaller size, they also occupy a larger diameter of the fixed hub 10. Thus an optimum number of struts 12 may depend on the specific patient and application.

The fixed hub 10 acts to prevent twisting or crossing of struts 12 during implantation and recovery procedures. Fixed hub 10 secures the fixed ends 14 of struts 12 together in a compact bundle to define a central or longitudinal axis X of the filter. The fixed hub 10 has a minimal diameter for the size of wire used to form the struts. Preferably, the struts 12 are formed from stainless steel wire, MP35N, Nitinol, or any other suitable superelastic material that will result in a self-opening or self-expanding filter. In this embodiment, the struts 12 are formed from wire having a round cross-section with a diameter of about 0.015 inches. Of course, it is not necessary that the struts 12 have a round cross-section. For example, the struts 12 could have a square shaped or other suitable shaped cross section without falling beyond the scope or spirit of the present invention. The fixed hub may be formed from steel or any other biocompatible metal or from a suitable plastic material.

Each strut 12 is formed with a first curved portion 13 that is configured to bend away from the longitudinal or central axis X of the filter 20 and a second curved portion 15 that is configured to bend toward the longitudinal axis of the filter 20. Each strut 12 maintains a non-parallel relationship with the longitudinal axis X of the filter 20. Opposite the fixed ends 14, the struts 12 terminate at anchoring hooks 22 that will anchor in the vessel wall when the filter 20 is deployed at a delivery location in the blood vessel. When the filter 20 is deployed, the anchoring hooks 22 define a radial plane in which the filter 20 is secured in the blood vessel. The anchoring hooks 22 prevent the filter 20 from migrating from the delivery location in the blood vessel where it has been deposited. The struts 12 are shaped and dimensioned such that, when the filter 20 is deployed and expanded, the filter 20 has a diameter of about 35 mm and a length of about 5 cm. For example, when expanded, the filter 20 may have a diameter of between about 30 mm and 40 mm, and a length of between about 3 cm and 7 cm. The struts 12 have sufficient spring strength that when the filter is deployed, the anchoring hooks 22 will securely engage the vessel wall.

The fixed hub 10 maintains the struts 12 in their preset configuration with respect to one another. In the shown embodiment, the fixed hub 10 includes a tubular portion 16 and a radially protruding annular collar 18 adjacent the tubular portion 16 opposite the struts 12. The term "tubular portion" is used in the broad sense of having a generally cylindrical shape. Alternatively, the tubular portion 16 of the fixed hub 10 may be solid without a central lumen.

A sleeve-shaped movable hub 24 surrounds the tubular portion 16 and abuts the annular collar 18 in a first position. The movable hub 24 is dimensioned to have a close fit around the tubular portion 16 so that it does not slip off the tubular portion 16 absent an external pulling force. The movable hub may be made of the same material as the fixed hub or a different biocompatible material that does not exhibit a chemical reaction with any other material used.

The annular collar 18 acts as a stopper that prevents the movable hub from slipping off the fixed hub 10 on the axial side of the annular collar 18. It is evident that any radial protrusion capable of keeping the movable hub 24 from sliding of the fixed hub 10 is suitable for this purpose, for example, single protruding noses distributed around the circumference of the tubular portion 16. Furthermore, an inward projection on the opposite end of the movable hub 24 would be suitable as well as a stopper abutting the axial end of the tubular portion 16 in the shown expanded configuration.

Secured on the movable hub 24 are a femoral hook 26 and a jugular hook 28. The femoral hook 26 extends to the axial side of the struts 12 and is configured to engage with a snare introduced through the femoral vein for femoral retrieval of filter 20, as will be explained in greater detail in connection with FIG. 3. The femoral hook 26 is preferably longer than the struts 12 for facilitating the engagement of the snare with the femoral hook 26 and for reducing the risk of entangling the snare with the struts 12. The jugular hook 28 extends axially past the collar 18 and is configured to engage with a snare introduced through the jugular vein for jugular retrieval of the filter 20. In the embodiment shown, the jugular hook is attached to a radial projection 30 for attaining a radial position outside the collar 18. Alternatively, the collar 18 may have a radial void (not shown) for the jugular hook 28 attached to the movable hub 24. If individual protrusions are provided instead of the collar 18, the jugular hook 28 can axially extend through the space between two protrusions. The jugular hook has 28 an axial dimension that corresponds approximately to an axial distance that the movable hub is intended to travel along the struts 12.

The delivery process and the jugular retrieval process are generally known in the art. For deployment of the filter 20, a delivery tube (not shown) is percutaneously inserted through the patient's vessels such that the distal end of the delivery tube is at the location of deployment. For example, a wire guide (not shown) can be used to guide the delivery tube to the location of deployment. The filter is preferably inserted through the proximal end of the delivery tube with the jugular hook 28 leading and the struts 12 trailing. During delivery, the struts 12 are optionally collapsed by moving the movable hub 24 along the struts 12 until the jugular hook 28 abuts the collar 18. For a more complete disclosure of a filter delivery system that may be used to deliver the filter 20 to a desired location, reference may be made to U.S. Pat. No. 5,324,304 and to U.S. Published Application No. 2010/01609954, which are incorporated herein by reference.

For jugular retrieval, a removal catheter or sheath (not shown) of a retrieval device is inserted into the superior vena cava. A wire with a loop snare (not shown) at its distal end is threaded through the recovery sheath and is exited through the distal end of the sheath. The wire is then manipulated by any suitable means from the proximal end of the retrieval device such that the loop snare captures the jugular hook 28 of the filter 20. Using counter traction by pulling the wire while pushing the sheath, the sheath is passed over the filter. As the sheath passes over the filter 20, the struts 12 engage the edge of the sheath and are caused to pivot at the hub 10 toward the longitudinal axis X of the filter 20. The pivoting movement toward the longitudinal axis X causes the anchoring hooks 22 of the struts 12 to be retracted from the vessel wall. In this way, only small point lesions on the vessel wall are created in the removal procedure. Because the jugular hook 28 is affixed to the movable hub 24, the movable hub 24 remains on the tubular portion 16 of the fixed hub 10 in the first position. Notably, any other suitable procedure may be implemented to remove the filter 20 from the patient. A more detailed description of a jugular removal process may be found in U.S. Published Application No. 2010/0160954, which is incorporated herein by reference.

Figure 3:
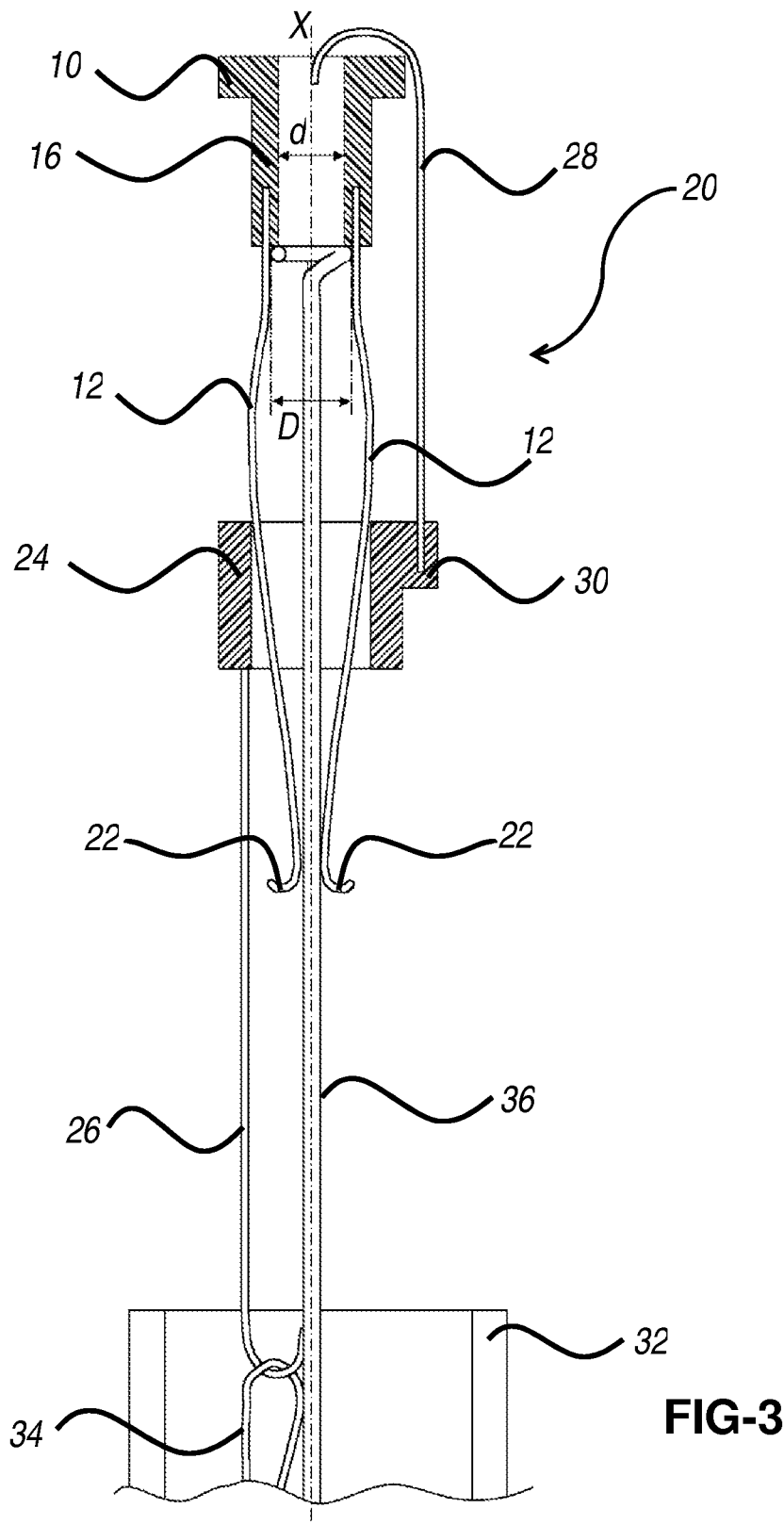
FIG. 3 is a cross-sectional view of the vena cava filter FIG. 2 in a collapsed configuration during femoral removal.

Now making reference to FIG. 3, the movable hub 24 allows a physician to approach the deployed filter 20 from the femoral side and collapse the struts 12 such that the filter 20 can be captured within a recovery sheath 32 and retrieved from the patient's body. A snare 34 located at the distal end of a flexible rod (not shown) can be inserted within the lumen of the recovery sheath 32 and may be utilized to engage the femoral hook 26 and displace the movable hub 24 along the struts 12. During this step, the fixed hub 10 is not intended to move. To ensure that the fixed hub 10 remains at its axial location while the movable hub 24 is pulled along the struts 12, a push tool 36 may be used to hold the fixed hub 10 in place. The push tool 36 may be inserted through the recovery sheath 32 and be placed proximate the fixed hub 10 before the snare 34 engages the femoral hook 26 or after the snare 34 engages the femoral hook 26.

Where, as in the shown embodiment, the fixed hub 10 has an axial lumen, the push tool has a tip 38 with a radial diameter D that exceeds the diameter d of the lumen of the fixed hub 10, but smaller than the distance of opposing struts 12 from each other adjacent the fixed hub 10. For embodiments in which the fixed hub 10 has a solid tubular portion 16, any push wire may be used to retain the fixed hub 10 in its axial position because a smaller abutment diameter is also suited for retaining the fixed hub 10 where the tubular portion 14 is solid.

The displacement of the movable hub 24 toward the hooks 22 forces the struts 12 to radially collapse toward the longitudinal axis X of the filter 20. The radially inward movement of the struts 12 disengages the anchoring hooks 22 from the vessel wall. The axial movement of the movable hub 24 along the struts 12 is limited by the axial length of the jugular hook 28. The jugular hook 28 is bent radially inward so that its free end abuts the fixed hub 10 once the jugular hook 28 has moved by a distance corresponding to the distance between its end and the fixed hub 10 in the expanded configuration shown in FIG. 2. Notably, the movable hub does not need to travel all the way to the anchoring hooks 22. It is sufficient that the movable hub 24 travels past the first curved portion 13 of the struts 12 (shown in FIG. 2). The second curved portion 13 providing the inward bend then provides that the struts 12 approach the longitudinal axis X without a further axial movement of the movable hub 24.

At this stage of the removal process, the push tool 36 is not needed any more. Thus, the push tool 36 may be removed separately, or it may be moved in the proximal direction along with the filter 20.

Once the struts 12 adjoining the recovery sheath 32 have been collapsed, the filter 20 can either be pulled proximally into the recovery sheath 32, or the recovery sheath 32 can be advanced distally to capture the filter 20 within the lumen of the recovery sheath 32. A more detailed description of a removal procedure with collapsed struts may be found in U.S. Pat. No. 8,029,529, which is incorporated herein by reference.

As described above, the jugular hook 28 has a dual function. It operates as a coupling member for jugular removal and as a retainer for femoral removal of the filter 20. It is well within the scope of the present invention to implement coupling members other than hooks. Also, the jugular coupling member may not have the dual function. The retaining function may be attained by different elements. For example, retaining elements include but are not limited to beads on the struts or an axially extending hook fastened on the fixed hub 10 on the axial side of the struts 12, where the hook is bent outward to catch the movable hub 24 when the movable hub reaches its intended travel distance.

As one skilled in the art having the benefit of this disclosure would appreciate, different materials, joining methods, and configurations may be implemented in manufacturing the filter.

While the present invention has been described in terms of preferred embodiments, it will be understood, of course, that the invention is not limited thereto since modifications may be made to those skilled in the art, particularly in light of the foregoing teachings.

What is claimed is:

1. An intravascular filter assembly having an expanded state for capturing thrombi in a patient's blood vessel and a collapsed state for removal from the patient's blood vessel, the filter assembly comprising:
   a fixed hub defining a tubular portion, the tubular portion having a second axial side comprising a stopper;
   a plurality of struts extending from a first axial side of the tubular portion of the fixed hub, the struts having an expanded configuration when the filter is in the expanded state and a collapsed configuration when the filter is in the collapsed state;
   an axially movable hub having a first position radially surrounding at least an axial portion of the tubular portion and a second position axially spaced apart from the fixed hub along the struts, the struts being in the collapsed configuration when the movable hub is in the second position, the stopper disposed outside of the movable hub;
   a first coupling member extending from a first axial side of the movable hub; and
   a second coupling member extending from a second axial side of the movable hub opposite the first axial side of the movable hub.

2. The filter assembly of claim 1, wherein the stopper prevents the movable hub from moving past the tubular portion on the second axial side.

3. The filter assembly of claim 1, wherein the stopper is an annular collar formed on the fixed hub adjacent the tubular portion.

4. The filter assembly of claim 1, further comprising a retainer limiting a distance of travel of the movable hub along the struts.

5. The filter assembly of claim 4, wherein the retainer is formed by a jugular hook forming the second coupling member.

6. The filter assembly of claim 5, wherein the jugular hook has an axial length determining the second position of the movable hub.

7. the filter assembly of claim 5, wherein the jugular hook extends axially from a radially outward projection formed on the movable hub.

8. The filter assembly of claim 1, wherein each of the struts has a first curved portion bending the strut away from a longitudinal axis of the filter and a second curved portion bending the strut toward the longitudinal axis of the filter.

9. The filter assembly of claim 8, wherein the second position of the movable hub is at least as far away from the fixed hub as the first curved portion of each strut.

10. The filter assembly of claim 1, wherein the stopper allows the movable hub to move up to only the second axial side of the tubular portion.

11. The filter assembly of claim 1, wherein the fixed hub comprises an axial passage formed from the first axial side of the tubular portion to the second axial side of the tubular portion.

12. An intravascular filter assembly having an expanded state for capturing thrombi in a patient's blood vessel and a collapsed state for removal from the patient's blood vessel, the filter assembly comprising:
    a fixed hub defining a tubular portion having a first axial side extending to a second axial side the fixed hub comprises an axial passage formed from the first axial side of the tubular portion to the second axial side of the tubular portion;
    a plurality of struts extending from the first axial side of the tubular portion of the fixed hub, the struts having an expanded configuration when the filter is in the expanded state and a collapsed configuration when the filter is in the collapsed state;
    an axially movable hub having a first position radially surrounding at least an axial portion of the tubular portion and a second position axially spaced apart from the fixed hub along the struts, the struts being in the collapsed configuration when the movable hub is in the second position;
    a first coupling member extending from a first axial side of the movable hub;
    a second coupling member extending from a second axial side of the movable hub opposite the first axial side of the movable hub; and
    a stopper disposed outside of the movable hub.

13. The filter assembly of claim 12, further comprising an elongated push tool with a tip having a diameter greater than the axial passage and smaller than a distance of opposing struts adjacent the fixed hub.

14. A method of removing an intravascular filter assembly from a body vessel, the filter assembly having a fixed hub defining a tubular portion, the tubular portion having a second axial side comprising a stopper; a plurality of struts extending from a first axial side of the tubular portion of the fixed hub, the struts having an expanded configuration when the filter is in an expanded state and a collapsed configuration when the filter is in a collapsed state; an axially movable hub having a first position radially surrounding at least an axial portion of the tubular portion and a second position axially spaced apart from the fixed hub along the struts, the struts being in the collapsed configuration when the movable hub is in the second position, the stopper disposed outside of the movable hub; a first coupling member extending from a first axial side of the movable hub; and a second coupling member extending from a second axial side of the movable hub opposite the first axial side of the movable hub; the method comprising the steps of:
    inserting a recovery sheath with a lumen into the body vessel from the first axial side;
    placing a recovery tool within the lumen of the recovery sheath and moving it distally toward the filter assembly;
    engaging the first coupling member with the recovery tool;
    placing a push tool within the lumen of the recovery sheath and moving it distally toward the filter assembly;
    abutting and retaining the fixed hub at a fixed location;
    pulling the movable hub off the tubular portion along the struts until the movable hub is in the second position and the struts are in the collapsed configuration;
    proximally removing the push tool;
    causing a relative movement between the filter assembly and the recovery sheath in a direction that causes the filter assembly to enter the lumen of the recovery sheath; and
    proximally removing the recovery sheath including the filter assembly.

15. The method of claim 14, wherein the push tool and the recovery sheath are removed simultaneously.

16. The method of claim 14, wherein the filter assembly further includes a retainer limiting a movement of the movable hub along the struts and thereby defining the second position of the movable hub, wherein the movable hub is moved until the retainer limits the movement.

17. The method of claim 16, wherein the retainer is a jugular hook limiting the movement by abutting the fixed hub.

18. An intravascular filter assembly having an expanded state for capturing thrombi in a patient's blood vessel and a collapsed state for removal from the patient's blood vessel, the filter assembly comprising:
    a fixed hub defining a tubular portion having a first axial side of the tubular portion and a second axial side of the tubular portion, the fixed hub comprises an axial passage formed from the first axial side of the tubular portion to the second axial side of the tubular portion;
    a plurality of struts extending from the first axial side of the tubular portion of the fixed hub, the struts having an expanded configuration when the filter is in the expanded state and a collapsed configuration when the filter is in the collapsed state;
    an axially movable hub having a first position radially surrounding at least an axial portion of the tubular portion and a second position axially spaced apart from the fixed hub along the struts, the struts being in the collapsed configuration when the movable hub is in the second position;
    a first coupling member extending from a first axial side of the movable hub;
    a second coupling member extending from a second axial side of the movable hub opposite the first axial side of the movable hub; and
    a stopper preventing the movable hub from moving past the tubular portion on the second axial side.

19. The filter assembly of claim 18, further comprising an elongated push tool with a tip having a diameter greater than the axial passage and smaller than a distance of opposing struts adjacent the fixed hub.

20. The filter assembly of claim 18, wherein the stopper is an annular collar formed on the fixed hub.

* * * * *